United States Patent [19]

Botstein et al.

[11] Patent Number: 4,695,470

[45] Date of Patent: Sep. 22, 1987

[54] RENNIN-CONTAINING DISRUPTED YEAST CELLS USED IN CHEESE MANUFACTURE

[75] Inventors: David Botstein, Brookline; Gerald R. Fink, Wellesley, both of Mass.; Ronald W. Davis, Menlo Park, Calif.

[73] Assignee: Collaborative Research, Inc., Bedford, Mass.

[21] Appl. No.: 471,360

[22] Filed: Feb. 28, 1983

[51] Int. Cl.$^4$ .............................................. A23C 9/12
[52] U.S. Cl. ...................................... 426/37; 426/34; 426/36; 426/40
[58] Field of Search ................... 426/34, 36, 37, 583, 426/63; 435/941, 942, 943, 223, 224, 267, 270, 272

[56] References Cited

U.S. PATENT DOCUMENTS

| | | | |
|---|---|---|---|
| 4,007,283 | 2/1977 | Crisan et al. | 426/34 |
| 4,218,481 | 8/1980 | Chao et al. | 426/62 |
| 4,285,976 | 8/1981 | Akin et al. | 435/267 |
| 4,432,997 | 2/1982 | Reimerdes | 426/34 |
| 4,435,431 | 3/1984 | Akatsuka | 426/34 |

*Primary Examiner*—Sam Rosen
*Attorney, Agent, or Firm*—Wolf, Greenfield & Sacks

[57] ABSTRACT

Yeast cells that express rennin or prorennin are used in disrupted cellular form to clot milk without the need for purification of the rennin or prorennin. Cheese making is simplified and reduced in cost by the avoidance of substantial purification techniques to obtain rennin or prorennin from living cells which produce these materials.

11 Claims, No Drawings

RENNIN-CONTAINING DISRUPTED YEAST CELLS USED IN CHEESE MANUFACTURE

BACKGROUND OF THE INVENTION

A large variety of cheeses are produced by clotting raw or pasteurized milk using acid, rennin or both. In the past, the rennin used is often obtained from rennet. This rennin is in nature an enzymatic protein used for coagulating milk casein in cheese making. It also acts as a cheese ripening material in the latter stages of cheese making through its proteolytic activity. Rennet has in the past been obtained from butchered milk-fed calves' stomachs processed in accordance with known techniques.

More recently, rennin or prorennin has been formed by recombinant DNA techniques, see for example European patent publication No. 82 110 124.5 filed Jan. 8, 1982 Publication No. 0057,350,A3 dated Aug. 11, 1982 Bulletin 82/32.

In the past, it has been suggested that where rennin or prorennin is produced from cellular materials, purification should be carried out to obtain the purified enzymatic material capable of activation to have milk clotting activity.

SUMMARY OF THE INVENTION

According to the invention, a method of clotting milk to form cheese comprises providing an active rennin enzyme along with disrupted yeast cells from which the rennin has been obtained, in a milk-based mixture to clot the milk. Preferably, the milk is clotted in the presence of an acid such as lactic acid. In the most preferred form, the yeast cells are those which produce a prorennin material which is activated to have rennin activity.

A resulting cheese product contains disrupted yeast cellular material obtained from yeast cells that express rennin or prorennin. The cellular material as well as the rennin remain in the cheese without substantially adversely affecting the edible nature of the cheese.

In some forms of the invention, the cell membranes can be removed from the yeast cells after they are disrupted while in other cases, the entire disrupted cell is employed by addition to the cheese making batch.

It is a feature of this invention that no separation of rennin or prorennin is required with the producer cells themselves capable of being added directly to the cheese making process. The disruption of the cells aids in freeing the rennin and prorennin materials. The materials can be activated to have rennin enzymatic activity in the presence of the yeast cells with or without the addition of acid. Taste and edibility of resulting cheese can be good with no adverse effects imparted to cheese made employing the methods and materials of the present invention.

It is an object of this invention to provide a means and method for clotting milk in a cheese making process using disrupted cellular material having contained therewith active rennin enzyme from said cellular material.

Still another object of this invention is to provide a method of clotting milk in an efficient manner with minimized separation of material having rennin activity from yeast cells which produce said material.

Still another object of this invention is to provide a cheese producting containing disrupted yeast cellular material from yeast cells that express rennin or prorennin.

DESCRIPTION OF THE PREFERRED EMBODIMENTS

The yeast cells which are used in the process of clotting milk in cheese making in accordance with the present invention can be any yeast cells which can be transformed with DNA as for example species of Saccharamyces such as *Saccharomyces cerevisiae*, *Saccharomyces carlsbergensis* and *Saccharomyces uvarum*, species of Saccharomycopsis such as *Saccharomycopsis lipolytica* and species of Schizosaccharomyces such as *Schizosaccharomyces pombe*. Transformable yeasts are those into which can be introduced foreign vectors with any known recombinant DNA and which produces yeast progeny that carry the vectors. Any such yeast cells which contain recombinant material that expresses rennin or prorennin, and clots milk can be used in connection with the method and products of this invention.

Such yeast cells contain DNA materials as for example that shown in Table 1 where the rennin gene is shown at nucleotide 379 to 1350. Several precursors thereof are broadly referred to as "prorennin" herein wich is defined here as precursor forms of rennin having additional amino acids at the amino terminus of rennin, which can be removed to yield an active rennin enzyme which clots milk. Preferably the plurality of nucleotide bases before the 5' end of the rennin are in the range of from 1 to 174 bases. "Prorennin" as used herein is shown in Table 1 at nucleotide 205 to 1350.

TABLE 1

| | | | | | | | | 30 | | | | | |
|---|---|---|---|---|---|---|---|---|---|---|---|---|---|
| AAG | CTT | GOG | OGA | GOG | AGG | GGT | AGG | OCA | TCC | OCA | GGA | TCC | CGT | OGA |
| | | | | 60 | | | | | | | | | | 90 |
| ATT | OGG | CAT | AGG | TGA | AGA | CGT | OCC | OGG | GCT | OCT | GGG | TGC | TCA | GGC |
| | | | | | | | | 120 | | | | | |
| CTA | CTG | TCT | GCT | GGA | TGT | OCA | CAA | TGT | TGG | AGA | CAG | TGA | OGG | TGT |
| | | | | 150 | | | | | | | | | | 180 |
| CAT | AGC | OCA | GGA | TGC | OCT | GCA | TGC | TGC | CTG | TCC | OGT | AGT | GGA | TAG |
| | | | | | | | | 210 | | | | | |
| ACA | GOG | GCT | GGA | COC | AGA | TCC | AAG | ATG | AGG | TGT | CTC | GTG | GTG | CTA |
| | | | | | | | | MET | ARG | CYS | LEU | VAL | VAL | LEU |
| | | | | 240 | | | | | | | | | | 270 |
| CTT | GCT | GTC | TTC | GCT | CTC | TCC | CAG | GGC | GCT | GAG | ATC | ACC | AGG | ATC |
| LEU | ALA | VAL | PHE | ALA | LEU | SER | GLN | GLY | ALA | GLU | ILE | THR | ARG | ILE |

300

TABLE 1-continued

| OCT PRO | CTG LEU | TAC TYR | AAA LYS | GGC GLY | AAG LYS | TCT SER | CTG LEU | AGG ARG | AAG LYS | GOG ALA | CTG LEU | AAG LYS | GAG GLU | CAT HIS |
|---|---|---|---|---|---|---|---|---|---|---|---|---|---|---|
| GGG GLY | CTT LEU | CTG LEU | GAG GLU | 330 GAC ASP | TTC PHE | CTG LEU | CAG GLN | AAA LYS | CAG GLN | CAG GLN | TAG TYR | GGC GLY | ATC ILE | 360 AGC SER |
| AGC SER | AAG LYS | TAC TYR | TCC SER | GGC GLY | TTC PHE | GGG GLY | GAG GLU | GTG VAL | 390 GOC ALA | AGC SER | GTG VAL | COC PRO | CTG LEU | AOC THR |
| AAC ASN | TAC TYR | CTG LEU | GAT ASP | 420 AGT SER | CAG GLN | TAC TYR | TTT PHE | GGG GLY | AAG LYS | ATC ILE | TAC TYR | CTC LEU | GGG GLY | 450 ACC THR |
| OCG PRO | COC PRO | CAG GLN | GAG GLU | TTC PHE | ACC THR | GTG VAL | CTG LEU | TTT PHE | 480 GAC ASP | ACT THR | GGC GLY | TOC SER | TCT SER | GAC ASP |
| TTC PHE | TGG TRP | GTA VAL | COC PRO | 510 TCT SER | ATC ILE | TAC TYR | TGC CYS | AAG LYS | AGC SER | AAT ASN | GOC ALA | TGC CYS | AAA LYS | 540 AAC ASN |
| CAC HIS | CAG GLN | OGC ARG | TTC PHE | GAC ASP | OCG PRO | AGA ARG | AAG LYS | TOG SER | 570 TOC SER | ACC THR | TTC PHE | CAG GLN | AAC ASN | CTG LEU |
| GGC GLY | AAG LYS | COC PRO | CTG LEU | 600 TCT SER | ATC ILE | CAC HIS | TAC TYR | GGG GLY | ACA THR | GGC GLY | AGC SER | ATG MET | CAG GLN | 630 GGC GLY |
| ATC ILE | CTG LEU | GGC GLY | TAT TYR | GAC ASP | ACC THR | GTC VAL | ACT THR | GTC VAL | 660 TOC SER | AAC ASN | ATT ILE | GTG VAL | GAC ASP | ATC ILE |
| CAG GLN | CAG GLN | ACA THR | GTA VAL | 690 GGC GLY | CTG LEU | AGC SER | ACC THR | CAG GLN | GAG GLU | COC PRO | GGG GLY | GAC ASP | GTC VAL | 720 TTC PHE |
| ACC THR | TAT TYR | GOC ALA | GAA GLU | TTC PHE | GAC ASP | GGG GLY | ATC ILE | CTG LEU | 750 GGG GLY | ATG MET | GOC ALA | TAC TYR | COC PRO | TOG SER |
| CTC LEU | GOC ALA | TCA SER | GAG GLU | 780 TAC TYR | TOG SER | ATA ILE | COC PRO | GTG VAL | TTT PHE | GAC ASP | AAC ASN | ATG MET | ATG MET | 810 AAC ASN |
| AGG ARG | CAC HIS | CTG LEU | GTG VAL | GOC ALA | CAA GLN | GAC ASP | CTG LEU | TTC PHE | 840 TOG SER | GTT VAL | TAC TYR | ATG MET | GAC ASP | AGG ARG |
| AAT ASN | GGC GLY | CAG GLN | GAG GLU | 870 AGC SER | ATG MET | CTC LEU | ACG THR | CTG LEU | GGG GLY | GOC ALA | ATC ILE | GAC ASP | CCG PRO | 900 TCC SER |
| TAC TYR | TAC TYR | ACA THR | GGG GLY | TOC SER | CTG LEU | CAC HIS | TGG TRP | GTG VAL | 930 OCC PRO | GTG VAL | ACA THR | GTG VAL | CAG GLN | CAG GLN |
| TAC TYR | TGG TRP | CAG GLN | TCC PHE | 960 ACT THR | GTG VAL | GAC ASP | AGT SER | GTC VAL | ACC THR | ATC ILE | AGC SER | GGT GLY | GTG VAL | 990 GTT VAL |
| GTG VAL | GOC ALA | TGT CYS | GAG GLU | GGT GLY | GGC GLY | TGT CYS | CAG GLN | GCC ALA | 1020 ATC ILE | CTG LEU | GAC ASP | ACG THR | GGC GLY | ACC THR |
| TOC SER | AAG LYS | CTG LEU | GTC VAL | 1050 GGG GLY | COC PRO | AGC SER | AGC SER | GAC ASP | ATC ILE | CTC LEU | AAC ASN | ATC ILE | CAG GLN | 1080 CAG GLN |
| GOC ALA | ATT ILE | GGA GLY | GOC ALA | ACA THR | CAG GLN | AAC ASN | CAG GLN | TAC TYR | 1110 GAT ASP | GAG GLU | TTT PHE | GAC ASP | ATC ILE | GAC ASP |
| TGC CYS | GAC ASP | AAC ASN | CTG LEU | 1140 AGC SER | TAC TYR | ATG MET | COC PRO | ACT THR | GTG VAL | GTC VAL | TTT PHE | GAG GLU | ATC ILE | 1170 AAT ASN |
| GGC GLY | AAA LYS | ATG MET | TAC TYR | OCA PRO | CTG LEU | ACC THR | COC PRO | TCC SER | 1200 GOC ALA | TAT TYR | ACC THR | AGC SER | CAG GLN | GAC ASP |

TABLE 1-continued

| | | | | 1230 | | | | | | | | | | 1260 |
|---|---|---|---|---|---|---|---|---|---|---|---|---|---|---|
| CAG | GGC | TTC | TGT | ACC | AGT | GGC | TTC | CAG | AGT | GAA | AAT | CAT | TCC | CAG |
| GLN | GLY | PHE | CYS | THR | SER | GLY | PHE | GIN | SER | GLU | ASN | HIS | SER | GLN |
| | | | | | | | | | 1290 | | | | | |
| AAA | TGG | ATC | CTG | GGG | GAT | GTT | TTC | ATC | OGA | GAG | TAT | TAC | AGC | GTC |
| LYS | TRP | ILE | LEU | GLY | ASP | VAL | PHE | ILE | ARG | GLU | TYR | TYR | SER | VAL |
| | | | | 1320 | | | | | | | | | | 1350 |
| TTT | GAC | AGG | GCC | AAC | AAC | CTC | GTG | GGG | CTG | GOC | AAA | GOC | ATC | TGA |
| PHE | ASP | ARG | ALA | ASN | ASN | LEU | VAL | GLY | LEU | ALA | LYS | ALA | ILE | |
| | | | | | | | | | 1380 | | | | | |
| TCA | CAT | OGC | TGA | OCA | AGA | ACC | TCA | CTG | TOC | OCA | CAC | ACC | TGC | ACA |
| | | | | 1410 | | | | | | | | | | 1440 |
| CAC | ACA | TGC | ACA | CAT | GTA | CAT | GGC | ACA | TGT | GCA | CAC | ACA | CAG | ATG |
| AGG | TTT | OCA | GAC | OCA | TT | | | | | | | | | |
| | | | | AGC | | | | | | | | | | |

Yeast cells which can be used in accordance with the present invention include microorganisms such as *Saccharomyces cerevisiae* identified as Accession No. 20623 deposited in the American Type Culture Collection of 12301 Park Warren Drive, Rockville, Md. 20852 by Collaborative Research, Inc.

The preferred yeast microorganism useful in this invention insofar as known to date is yeast cells deposited as Accession No. 20662 which is a strain of *Saccharomyces cerevisiae* deposited in the American Type Culture Collection of 12301 Park Warren Drive, Rockville, Md. 20852 in February of 1983 which expresses prorennin which can be activated to rennin. The prorennin is expressed in an amount of about 0.2% by weight of all soluble protein expressed by the cells.

The yeast cells can be grown in conventional yeast media under conventional yeast growing conditions. For example, common laboratory media known for producing yeast under relatively uniform conditions can be used. Usual growth requirements of yeast include:

(a) organic carbon compound for carbon and energy;
(b) organic or inorganic nitrogen for the synthesis of proteins and nucleic acids;
(c) various minerals (including compounds furnishing trace elements); and
(d) frequently a mixture of vitamins.

Such growth requirements are met by yeast nitrogen base (YNB, obtained from Difco Company of Detroit, Mich.), a chemically defined medium which contains a number of trace elements, 9 vitamins, trace amounts of amino acids to stimulate growth of certain fastidious yeasts and the principal minerals, potassium phosphate, magnesium sulfate, sodium chloride, and calcium chloride. The nitrogen source is ammonium sulfate. The desired carbon source must be added and is normally at a concentrations of 0.5-3% by weight. Additions can be made to this medium to fit particular strain requirements. The pH range of the medium is usually from pH 3-8. The preferred range is pH 4.5-6.5.

The yeast cells are grown under standard conditions as for example temperatures of from 20° to 35° C. as known in the art. The yeast cells can be grown in the culture media to cell densities consistent with maximizing production from the media involved. Often it is found that cells can be grown in the media to densities of from 30 to 100 Klett units corresponding to cells per ml of from 1 to $4 \times 10^7$ cells/ml. Preferably the cell density is from 50 to 70 Klett. The time periods of cells growth can vary greatly from two hours to several days as desired. Double times of from 2 to 10 hours are known for most yeast cells.

After the cells are grown in the media, they are preferably first separated from the media and resuspended in buffer prior to use in clotting milk in a cheese making operation. However, in some cases the media itself along with the cells can be treated to break the cell walls by mechanical agitation or enzymatic disruption with the resulting disrupted cells in the media itself added to milk in a cheese making operation.

Preferably, the cells are first removed from the media as by centrifugation harvesting at speeds at times which do not break the cells as for example rpms of from 1000 to 10,000 at times of from about 30 minutes to about 5 minutes respectively. The cells can also be separated from the media by filtration processes if desired.

The cells removed from the media can be stored in a pellet form or used immediately. Pellet forms can be frozen at −70° and stored for indefinite times.

Yeast cells containing the recombinant DNA material for expressing rennin or prorennin and preferably prorennin, are preferably suspended in a buffer prior to disruption of the cells. The buffer can be any conventional buffer including: sodium or potassium phosphate, Tris, sodium or potassium acetate. The buffer used where the cells are to be treated with acid for activation of the yeast-synthesized prorennin to obtain rennin activity is preferably in the range of from about pH 4 to about pH 9 and preferably pH 4.7 to 8.7. Where the cells are to be used without addition of acid, the buffer is preferably selected to have a pH in the range of 3.7 to 5.0.

The method of breaking the cells walls to form disrupted cells in accordance with the invention can vary. Preferably the cell walls and membranes of the yeast cells are broken by mechanical means although enzymatic disruption of the cell wall can be used. For example, vigorous agitation in the presence of glass beads of 250-450 micrometers in diameter (M. Rose, M. J. Casadaban & D. Botstein, 1981, *Proc. Nat'l. Acad. Sci. USA*, 78, 2460-2464) can be used to disrupt the yeast cells. The agitation can be by vortexing, centrifuging, stirring or otherwise agitating. Digestion with enzymes such as glusulase (L. Gaurente & M. Ptashne, 1981, *Proc. Nat'l Acad. Sci. USA*, 78, 2199-2203), lyticase (P. Novick, S. Ferro & R. Schekman, 1981, *Cell*, 25, 461–469) or zymolase (K. Kitamura & Y Yamamoto, 1981, *Agric. Biol. Chem.* (Japan), 45, 1761–1766) followed by transfer to low osmotic strength solution (K. Kitamura & Y. Yamamoto, supra) will disrupt yeast cells generating a crude extract.

The disrupted cell material includes cytoplasmic and nuclear material and the disrupted cell membranes and walls. However, in many cases, after mechanical breakage, centrifugation or filtering can be used to remove the cell debris, and the disrupted cellular material is used to clot milk with the cell debris, i.e., walls and membranes, removed. Commonly centrifugation at from 10,000 to 30,000 rpm for 30 minutes to 60 minutes will allow removal of the cell walls and membranes as a pellet from the disrupted cellular solutions. The terms "disrupted cellular material" and "disrupted yeast cells" as used herein mean and include all of the cellular material with the cell membranes and walls broken and include such materials with the cell membranes and walls removed as by filtration or centrifugation.

The following examples are illustrative of the invention showing the activation of prorennin made in yeast to given rennin activity in a milk clotting process for use in cheese making.

EXAMPLE I

Yeast strain CGY 461 (American Type Culture Collection Accession Number 20662) was grown from a single colony on an S-galactose plus leucine agar plate (some composition of liquid media below but also containing 1.5% agar) at 30° C. in 10 ml of S-galactose plus leucine liquid media (having per liter: 6.7 grams Difco yeast nitrogen base without amino acids which was sterilized by autoclaving at 120° C., 15 lbs. pressure for 30 minutes and then supplemented with 100 ml of 20% D-galactose obtained from Sigma Chemical Co. of St. Louis, Mo. and 33 mg L-leucine both of which had been autoclaved separately) to a density of Klett 100–200. A 500 ml culture of the same liquid media was then inoculated at a level of 2% with the smaller overnight culture above and allowed to grow about 15 hours at 30° C. in the liquid media described above until it had reached a Klett of 70. The yeast culture was then harvested in 50 ml aliquots by centrifugation at 7000 rpm for 10 minutes, washed once with distilled water and stored as a cell pellet frozen at $-70°$ C.

The prorennin in the yeast cells was activated to rennin as follows. Each frozen cell pellet, representing the cells from 50 ml of S-galactose plus leucine culture, was resuspended in 250 $\mu$l of buffer containing 50 mM Tris-Hcl ph 8.7, 10% glycerol, 4 mM (EDTA) ethylenediaminetetraacetic acid and the cells were disrupted by vortexing at top speed in a Genie Vortex Mixer made by Fisher Scientific Company of St. Louis, Mo., with 0.4 grams of nitric acid-washed and water-rinshed glass beads, having average diameters of 250 $\mu$m, for four one-minute periods with cooling on ice between cycles. The mass of disrupted cellular material was removed from the glass beads by pipette and transferred to another tube. Within a few minutes, 20 $\mu$l of 4M lactic acid was added to 200 $\mu$l of the crude cell extract, and the mixture was incubated at 25° C. for 60–90 minutes. After this incubation, which activated the prorennin to rennin, 3.3 $\mu$l of 6M NaOH was added to neutralize the mixture. This activated crude disrupted cellular material displays about 1.3 milliunits of milk clotting activity by a modification of the method of Foltmann (B. Foltmann, *Methods in Enzymology,* 19 421–436). The assays were done at 1/10 scale of Foltmann. Activated extracted (100–200 $\mu$l) was added to 1 ml of dried milk (12 g/100 ml) reconstituted in 10 mM $CaCl_2$ and incubated at 30° C. with shaking. One unit of rennin clots 1 ml milk in 10 seconds by this modified assay. The same procedure performed on the cells of the parent yeast strain containing no prorennin gene results in no detectable milk clotting activity. The buffer used can vary from a pH of 4.7 to 8.7 while the glycerol and EDTA can be eliminated. When the glass beads are changed, mechanical breakage can be carried out at various size beads but preferably the size is in the range of from 200 to 400 $\mu$m. The lactic acid used which is about pH 2, may be 4M to 6.5M and other acids can be used so long as the pH is about 2 to permit activation to the rennin activity desired.

EXAMPLE II

In a second specific example, yeast cells of strain CGY 461 (American Type Culture Collection Accession No. 20662) were grown, harvested and stored as in Example I above.

The prorennin in the yeast cells was activated to rennin without the addition of acid here. Each frozen cell pellet, representing the cells from 50 ml of S-galactose plus leucine culture was resuspended in 250 $\mu$l of 30 mM sodium acetate buffer at pH 4.7 and the cells were disrupted by vortexing at top speed in a "Genie Vortex Mixer" of Fisher Scientific Co. of St. Louis, Mo., with 0.4 grams nitric acid washed and water rinsed glass beads of average diameter 250 $\mu$m for 4 one-minute periods with cooling on ice between cycles. The crude disrupted cells were then removed from the glass beads by pipette and transferred to another tube. After incubation at 25° C. for one hour, 200 $\mu$l of the activated crude disrupted cellular material displayed 2 milliunits of milk clotting activity using a modificaton of the method of Foltmann as before (B. Foltmann, *Methods in Enzymology,* 19, 421–436). A similar extract from yeast cells containing no prorennin gene displayed no detectable milk clotting activity. Here the buffer used can range in pH from 3.7 to 5.0.

In a theoretical example of making cheese, cheddar cheese is made by substitution for the rennet preparation ordinarily used in a setting step, an equivalent amount of the disrupted cellular product prepared as in Example I. In this procedure, pasteurized whole milk is adjusted to 86°–88° F. and 1% by weight of a commercial lactic acid starter solution is added. The disrupted cellular material as obtained in Example I from 25 liters of culture is added for 10 liters of milk. The mixture is agitated until a curd of satisfactory firmness is obtained. The curd is cut into cubes and then cooked at 100° F. for several hours. The curd is separated from the whey and layered into slabs. The milled curd is then salted with 3% by weight of cheese salt. The salted curd can be transferred to hoops, pressed and then placed in a curing room. Cheese made from the rennin of this example can be sampled periodically after several days of curing and can be found to possess excellent qualities and be essentially free of unwanted flavors.

While specific embodiments of the present invention have been shown and described, many variations are possible. Other conventional methods of making cheddar cheese, for example, those described by Prescott and Dunn in "Industrial Microbiology", chapter 21 (3rd edition 1959), McGraw-Hill Book Co., Inc., New York and the references cited therein can be used in the practice of the present invention by substitution for the rennet preparations ordinarly employed in cheese making, an amount of the disrupted cellular material of the present invention containing an equivalent amount of rennet to produce quality cheese. The cheeses can be cheddar or any of the roughly eighteen varieties known.

The amount of disrupted cellular material used is preferably that which carries rennin activity units of rennin or prorennin in an amount equivalent to the rennin activity units of conventional rennin conventionally added to milk in cheese making procedures. For example, when making cheddar cheese, 130 Foltmann units of rennin activity in a volume of 50 ml to each 10 liters of milk is customarily used. However, the volume of Foltmann units can vary depending upon the particular cheese, the hardness of the cheese and other values in the final product desired. When the rennin activity units of the yeast cell used is maintained at about the level of conventional rennet, rennin activity levels as used in various cheese making operations, similar results can be obtained. For example, in making cheddar cheese, sufficient disrupted cells containing about 130 Foltmann units in each 50 ml of buffer for each 10 liters of milk to be clotted are used and yield desirable results are obtained in cheese making.

The cells of Example I when disrupted contain sufficient genetic material to provide at least 0.2% of the protein produced by such cells being prorennin with 0.025% rennin activity. However, desirably, yeast cells for use in the present invention have at least 0.5% of the protein produced by the yeast cells having rennin activity or being prorennin which can be activated to that level of rennin activity. Where the yeast cells used do not themselves have sufficient rennin activity as may be desired in a particular cheese making procedure, additional or supplementary naturally occurring or otherwise required rennin can be added to the process to enhance cheese making.

In the embodiment shown, cells from 16 liters of culture grown as in Example I are sufficient for clotting 10 liters of milk when all of the prorennin of the cells is activated to have rennin activity. When cells having 0.5% of protein with rennin activity are used, cells from 6.5 liters as grown in Example I clot 10 liters of milk. When the cells of Example I are used with only 0.025% of protein having rennin activity, the cells from 65 liters should be used to clot 10 liters of milk or supplementary rennin can be added along with small quantities of cells. Of course the amounts of cellular material and rennin used can vary greatly depending on the type of cheese desired and other parameters used and materials added in the cheese making operation.

What is claimed is:

1. A method of clotting milk to form cheese, said method comprising,
   providing an active rennin enzyme along with disrupted transformable yeast cells which contain recombinant material from which said rennin has been obtained, in a milk based mixture to clot said milk in the preparation of cheese.

2. A method in accordance with the method of claim 1 and further comprising said disrupted yeast cells having removed therefrom cell wall and membrane materials.

3. A method in accordance with the method of claim 1 wherein said yeast cells contain genetic materials as formed in CGY 461 American Type Culture Collection Accession No. 20662.

4. In a method of clotting milk for cheese preparation, the steps comprising, intermixing disrupted yeast cellular material from transformable yeast cells carrying a recombinant prorennin gene, with milk and heating to clot said milk without the addition of any acid material.

5. A method in accordance with the method of claim 1 and further comprising said prorennin gene having the sequence of nucleotide bases from number 205 to 1350 as described in Table 1.

6. In a method of clotting milk to form cheese, the improvement comprising,
   providing disrupted transformable yeast cells that contain recombinant material that expresses rennin or prorennin which can be used to clot milk,
   said disrupted yeast cells being provided in a buffer.

7. A method in accordance with the method of claim 6 wherein said buffer is buffered to a pH of from 4 to 9.

8. A method in accordance with the method of claim 7 wherein said disrupted cells having sufficient rennin activity so as to provide a rennin activity equal to the amount of rennet activity necessary to clot said milk when rennet from calves' stomachs is added to milk.

9. A cheese product comprising yeast cellular material from disrupted transformable yeast cells that contain recombinant material that expresses rennin or prorennin and a cheese product.

10. A cheese product in accordance with claim 9 wherein said cellular material is substantially all of the cellular material of said cells.

11. A cheese product in accordance with the product of claim 9 wherein cell walls and membranes have been removed from said disrupted cellular material.

* * * * *